(12) United States Patent
Taylor et al.

(10) Patent No.: US 8,795,700 B2
(45) Date of Patent: Aug. 5, 2014

(54) PYRIPROXYFEN COMPOSITIONS

(75) Inventors: Evelyn Jean Taylor, San Ramon, CA (US); Humberto Benito Lopez, Dublin, CA (US)

(73) Assignee: Valent U.S.A., Corporation, Walnut Creek, CA (US)

( * ) Notice: Subject to any disclaimer, the term of this patent is extended or adjusted under 35 U.S.C. 154(b) by 247 days.

(21) Appl. No.: 12/431,951

(22) Filed: Apr. 29, 2009

(65) Prior Publication Data

US 2009/0275601 A1    Nov. 5, 2009

Related U.S. Application Data

(60) Provisional application No. 61/048,974, filed on Apr. 30, 2008.

(51) Int. Cl.
| | |
|---|---|
| *A01N 25/04* | (2006.01) |
| *A01N 31/08* | (2006.01) |
| *A01N 43/40* | (2006.01) |
| *A61K 31/23* | (2006.01) |
| *A61K 31/44* | (2006.01) |

(52) U.S. Cl.
USPC ........... 424/405; 504/100; 504/254; 514/277; 514/345; 546/290; 546/301

(58) Field of Classification Search
USPC ............ 424/405; 514/277, 345; 546/290, 301
See application file for complete search history.

(56) References Cited

U.S. PATENT DOCUMENTS

| | | | | |
|---|---|---|---|---|
| 5,206,225 | A * | 4/1993 | Horstmann et al. | 514/63 |
| 6,274,570 | B1 * | 8/2001 | Vogt et al. | 514/89 |
| 6,296,864 | B1 | 10/2001 | Zen | |
| 6,635,663 | B1 * | 10/2003 | Zen | 514/345 |
| 2004/0063583 | A1 * | 4/2004 | Zen | 504/254 |
| 2005/0169951 | A1 | 8/2005 | Sasson et al. | |
| 2007/0244073 | A1 * | 10/2007 | Angst et al. | 514/86 |
| 2007/0270612 | A1 * | 11/2007 | Pompeo et al. | 564/123 |
| 2008/0096763 | A1 | 4/2008 | Dawson et al. | |

FOREIGN PATENT DOCUMENTS

| | | | | |
|---|---|---|---|---|
| EP | 0 933 025 A1 | | 8/1999 | |
| WO | WO96/01047 | * | 1/1996 | ............ A01N 25/02 |
| WO | WO 02/43488 A1 | | 6/2002 | |
| WO | WO 2005/107468 A1 | * | 11/2005 | |
| WO | WO 2007/081553 A2 | | 7/2007 | |

OTHER PUBLICATIONS

Office Action issued Jul. 1, 2013 in European counterpart.
Kluppelholz at al.,"Cognis innovation award for improved green solvent production processes", internet citation, Feb. 10, 2006, pp. 1-2.

\* cited by examiner

*Primary Examiner* — Jane C Oswecki
(74) *Attorney, Agent, or Firm* — Wood, Phillips, Katz, Clark & Mortimer

(57) ABSTRACT

New pesticidal compositions comprising pyriproxyfen and methyl esters of $C_{16}$-$C_{18}$ fatty acids and having low volatile organic compound (VOC) content are provided. Methods of use and ready-to-use products are also provided.

10 Claims, No Drawings

PYRIPROXYFEN COMPOSITIONS

FIELD OF THE INVENTION

The present invention generally relates to pesticidal compositions with low amounts of volatile organic compounds (VOCs).

BACKGROUND OF THE INVENTION

Insect growth regulators (e.g., pesticides) have enjoyed widespread use in commercial agriculture and have enabled an enormous increase in crop yields and product quality. Pesticides are also routinely used to control various insects, as for example flies or mosquitoes, when pest populations pose a nuisance or health hazard to humans or livestock.

One of the conventional formulations of a pesticide is an emulsifiable concentrate (EC). Such concentrates are later diluted prior to use. Some examples of such compositions are provided in U.S. Pat. No. 6,296,864 and U.S. Pat. No. 6,387,960.

Conventional EC formulations are typically made with solvents having high solvency for a large number of pesticides, such as aromatic hydrocarbon solvents. However, one of the disadvantages of aromatic hydrocarbon solvents is that they are considered volatile organic compounds (VOCs) and, therefore, are harmful to the environment. The United States Environmental Protection Agency (EPA) defines a VOC as an organic compound that participates in atmospheric photochemical reactions, but makes exceptions for compounds that have negligible photochemical reactivity. VOCs are emitted as gases from certain solids or liquids. They include a variety of chemicals, some of which may have short- and long-term adverse health effects. Conventional EC formulations generally contain 50-90% by weight VOCs.

There is, therefore, a need to identify effective insect growth regulator compositions that contain low amounts of VOCs.

BRIEF SUMMARY OF THE INVENTION

The present invention is generally directed to a low VOC pesticidal composition comprising from about 0.1% to about 30% by weight of pyriproxyfen (2-[1-methyl-2-(4-phenoxyphenoxy)ethoxy]pyridine); from about 1% to about 30% by weight of a surfactant; and from about 40% to about 90% by weight of methyl esters of $C_{16}$-$C_{18}$ fatty acids, wherein the weight percentages are based on the total weight of the pesticidal composition.

In a preferred embodiment, the low VOC pesticidal composition of the present invention is an emulsifiable concentrate (EC).

In a preferred embodiment, the surfactant comprises a blend of calcium alkylbenzenesulfonate and a fatty acid alkoxylate.

In one embodiment, the low VOC pesticidal composition of the present invention comprises a co-solvent. Preferably, the additional solvent is a disubstituted amide or ethyl hexyl lactate. Presently preferred co-solvents are ethyl hexyl lactate and N,N-dimethyloctanamide, N,N-dimethyldecanamide, or a blend thereof. In a preferred embodiment, the co-solvent prevents crystal formation in the compositions of the present invention.

In a preferred embodiment, the low VOC pesticidal composition of the present invention comprises from about 5% to about 20% by weight of pyriproxyfen; from about 5% to about 30% by weight of a surfactant; and from about 40% to about 80% by weight of methyl esters of $C_{16}$-$C_{18}$ fatty acids.

In a more preferred embodiment, the low VOC pesticidal composition of the present invention comprises about 11% by weight of pyriproxyfen; about 12% by weight of a surfactant; about 69% by weight of methyl oleate, and about 8% by weight of a fatty acid dimethylamide or ethyl hexyl lactate, wherein the weight percentages are based on the total weight of the pesticidal composition.

In yet another embodiment, the invention relates to a ready-to-use product prepared from the pesticidal compositions of the present invention.

In a preferred embodiment, the low VOC pesticidal compositions of the present invention comprise less than 20% by weight of volatile organic compounds.

In another embodiment, the invention relates to a method of treating plants, including genetically modified plants, comprising applying a pesticidally effective amount of a ready-to-use product prepared from the pesticidal compositions of the present invention to said plants and to a method of delivering pyriproxyfen to plants comprising applying pyriproxyfen to said plants as a low VOC emulsifiable concentrate comprising pyriproxyfen, a surfactant and a low VOC solvent.

DETAILED DESCRIPTION OF THE INVENTION

The present invention is generally directed to a low VOC pesticidal composition comprising from about 0.1% to about 30% by weight of pyriproxyfen (2-[1-methyl-2-(4-phenoxyphenoxy)ethoxy]pyridine); from about 1% to about 30% by weight of a surfactant; and from about 40% to about 90% by weight of methyl esters of $C_{16}$-$C_{18}$ fatty acids, wherein the weight percentages are based on the total weight of the pesticidal composition.

The term "pest" is defined as any living stage of any flying and crawling pest or plant pests.

As used herein, the term "surfactant" is defined as a surfactant or blend of surfactants.

The United States Environmental Protection Agency (EPA) defines a volatile organic compound (VOC) as an organic compound that participates in an atmospheric photochemical reaction, with the exception of compounds that have negligible photochemical reactivity. Long chain fatty acid methyl esters are not considered volatile organic compounds (VOCs).

Applicants surprisingly found that long chain fatty acid methyl esters, alone or in combination with a co-solvent may be used to prepare a pesticidal composition containing less than 20% volatile organic compounds. The compositions of the present invention have low VOC content; that is, they have low amounts of VOCs.

Accordingly, in a preferred embodiment, the pesticidal compositions of the present invention do not contain a significant amount of volatile organic compounds.

Thus, in a preferred embodiment, the pesticidal compositions of the present invention do not contain any significant amount of volatile organic compounds. The term "significant," as used in this context, means the amount of volatile organic compounds is less than 20%, and preferably less than 5% when no co-solvent is used.

Preferably, the pesticidal compositions of the present invention further comprise a co-solvent. Most preferably, the co-solvent helps to prevent crystals from forming in the compositions of the present invention after storage. The pesticidal composition may comprise more than one co-solvent.

Preferably, the co-solvent is a disubstituted amide or ethyl hexyl lactate. Presently preferred co-solvents are ethyl hexyl lactate and N,N-dimethyloctanamide, N,N-dimethyldecanamide, or a blend thereof. Other useful co-solvents include acetyl butyl citrate, butyl lactate, ethyl lactate, acetophenone, Aromatic 150, Aromatic 200, Solvesso 150 or Solvesso 200. Aromatic 150, Aromatic 200, Solvesso 150 and Solvesso 200 are aromatic hydrocarbon solvents available from ExxonMobil Chemical Company.

In a preferred embodiment, the pesticidal composition of the present invention is an emulsifiable concentrate (EC). The pesticidal composition of the present invention is usually used as a formulation for foliage treatment.

For foliage treatment, in general, stems and leaves are sprayed with a dilution prepared by diluting the composition of the present invention approximately 100- to 5,000-fold with water, though the degree of dilution may vary depending on the kind and content of the active ingredient in the present composition. It is also possible to carry out the aerial application of a dilution prepared by diluting the composition of the present invention approximately 10- to 1000-fold with water, by a helicopter or an airplane.

The surfactants used in the present invention can be both nonionic surfactant(s) and anionic surfactant(s) or a blend thereof.

In a preferred embodiment of the invention, the surfactant comprises a blend of calcium alkylbenzenesulfonate and a fatty acid alkoxylate.

In another embodiment of the invention, one or more nonionic surfactants are selected from the group consisting of alkoxylated triglycerides, alkoxylated fatty alcohols, alkoxylated tristyryl phenols, ethoxylated fatty acids, alkyl polyglycosides, fatty acid PEG esters, alkoxylated sorbitan esters, polyoxyethylene polyoxypropylene block polymers, polyoxyethylene polyoxypropylene alkyl aryl ethers, polyoxyethylene polyoxypropylene alkyl ethers, polyoxyethylene polyoxypropylene polyaryl ethers, polyoxyethylene fatty acid esters, and fatty acid esters of polyoxyethylene polyoxypropylene block polymers. The anionic surfactant(s) may be selected from the group consisting of alkoxylated tristyryl phenol phosphates, oleoyltaurate salts, polyacrylates, alkylarylsulfonic acid salts, dialkylsulfosuccinate salts, ether sulfates and phosphate esters.

Of the above-exemplified nonionic surfactants, those having a molecular weight of approximately 500-10,000 are preferable. More preferable are polyoxyethylene polyoxypropylene block polymers, polyoxyethylene polyoxypropylene alkyl aryl ethers (e.g. polyoxyethylene polyoxypropylene nonyl phenol ethers), polyoxyethylene polyoxypropylene alkyl ethers (e.g. polyoxyethylene polyoxypropylene butyl ethers), polyoxyethylene polyoxypropylene polyaryl ethers (e.g. tristyrylphenyl ethers of polyoxyethylene polyoxypropylenes, and distyrylphenyl ethers of polyoxyethylene polyoxypropylenes), polyoxyethylene fatty acid esters, and fatty acid esters of polyoxyethylene polyoxypropylene block polymers (e.g. stearic acid esters of polyoxyethylene polyoxypropylene block polymers).

Other suitable nonionic surfactants include ethoxylated castor oils, ethoxylated tridecyl alcohols, ethoxylated oleic acid, $C_8$-$C_{10}$ alkyl polyglycoside, polyoxyethylene alkylphenyl ethers, polyoxyethylene vegetable oils, polyoxyethylene hardened vegetable oils, polyoxyethylene tristyrylphenyl ethers, polyoxyethylene alkyl aryl ether polymers, polyoxyethylene alkyl ethers, polyoxyethylene distyrylphenyl ether polymers, polyoxyethylene tristyrylphenylphosphate diesters, polyoxyalkylphenol ethers, fatty acid alcohol polyglycol ethers, glycerol fatty acid esters, etc.

Of the above-exemplified anionic surfactants, alkylarylsulfonic acid salts are preferable. More preferable are calcium salts of alkylbenzenesulfonic acids. Most preferable are calcium salts of alkyl($C_{10}$-$C_{16}$)benzenesulfonic acids and calcium salts of dodecylbenzenesulfonic acid.

Other suitable anionic surfactants include sodium dioctyl sulfosuccinate, sodium di-(2-ethylhexyl) sulfosuccinate, sodium dihexyl sulfosuccinate, sodium dicyclohexyl sulfosuccinate, sodium diamyl sulfosuccinate, sodium diisobutyl sulfosuccinate, sodium ditridecyl sulfosuccinate, sodium or ammonium salts of fatty alcohol ether sulfates, sodium or ammonium salts of alkylaryl ether sulfates, sodium or ammonium salts of ethoxylated alkylaryl ether sulfates, polyoxyethylene tallow amine alkylphenol ether sulfates, polyoxyethylene tallow amine alcohol ether sulfate, polyoxyethylene tridecyl ether phosphate, polyoxyethylene lauryl ether phosphate, polyoxyethylene nonylphenol phosphate, polyoxyethylene isodecyl ether phosphate, polyoxyethylene dinonylphenol phosphate and polyoxyethylene 2-ethylhexyl ether phosphate.

The amount of the surfactant in the compositions of the present invention is from about 1% to about 30% by weight of the pesticidal composition; most preferably, from about 5% to about 20% by weight of the pesticidal composition.

Thus, another advantage of the pesticidal compositions of the present invention is that they can be stored for a long period of time retaining their pesticidal activity and emulsification properties, and without forming crystals.

In one embodiment, the pesticidal composition of the present invention retains most of its pesticidal activity and emulsification properties after being stored at ambient temperatures for 3 months. In a preferred embodiment, the pesticidal composition of the present invention retains most of its pesticidal activity and emulsification properties after being stored at ambient temperatures for 6 months, and in the most preferred embodiment, the pesticidal composition of the present invention retains most of its pesticidal activity and emulsion properties after being stored at 40° C. and 50° C. for at least nine months and at ambient temperatures for at least 24 months.

In one embodiment, the pesticidal composition of the present invention does not form a substantial number of crystals after being stored at −7° C. and ambient temperature for 15 months. A "substantial number" means such number of crystals that would substantially affect suitability of the pesticidal composition for commercial use and/or substantially lower its pesticidal activity.

In a preferred embodiment, the pesticidal composition of the present invention comprises from about 5% to about 20% by weight of pyriproxyfen; from about 5% to about 30% by weight of the surfactant; and from about 40% to about 80% by weight of methyl esters of $C_{16}$-$C_{18}$ fatty acids, wherein the weight percentages are based on the total weight of the pesticidal composition.

In a more preferred embodiment, the pesticidal composition of the present invention comprises about 11% by weight of pyriproxyfen; about 12% by weight of the surfactant; about 69% by weight of methyl esters of $C_{16}$-$C_{18}$ fatty acids, and about 8% by weight of a disubstituted amide or ethyl hexyl lactate solvent, wherein the weight percentages are based on the total weight of the pesticidal composition.

In another embodiment, the invention relates to a ready-to-use product prepared from the pesticidal compositions of the present invention. It is well within a skill of the art to prepare such ready-to-use products using well-known techniques, such as dilutions. The dilutions may be made in water. In one embodiment, the pesticidal compositions of the present invention are themselves ready-to-use products.

In yet another embodiment, the invention relates to a method of treating plants comprising applying a pesticidally effective amount of ready-to-use products prepared from the pesticidal compositions of the present invention. A person skilled in the art would readily know how to "treat" plants, as these techniques are well known in the art and are applicable to the compositions of the present invention.

The term "plants" is intended to be construed broadly. Plants that may be treated include, but are not limited to, cotton, citrus, pome fruit, stone fruit, tree nuts, grapes, brassica leafy vegetables, bushberries, cucurbits, and fruiting vegetables.

The phrase "pesticidally effective amount" of the formulation means a sufficient amount of the formulation to provide the desired effect. In general, the formulation is employed in amounts that do not cause phytotoxic damage to any part of the plant. The amount of the formulation may vary depending on specific crops and other factors. It is well within an ordinary skill in the art to determine the necessary amount of the formulation.

As used herein, all numerical values relating to amounts, weights, and the like, are defined as "about" or "approximately" each particular value, namely, plus or minus 10%. For example, the phrase "at least 5% by weight" is to be understood as "at least 4.5% to 5.5% by weight." Therefore, amounts within 10% of the claimed value are encompassed by the scope of the claims.

As used herein, "Pyriproxyfen Technical" contains 97-100% by weight pyriproxyfen.

The following Examples are intended to illustrate the present invention and to teach one of ordinary skill in the art how to make and use the invention. They are not intended to limit the invention in any way.

EXAMPLES

Example 1

A formulation was prepared by conventional blending techniques consisting of Pyriproxyfen Technical at about 20% by weight, methyl oleate at about 59% by weight, a tristyryl phenol ethoxylate with 16 moles of ethoxylation, Makon TSP 16, at about 11% by weight, and a disubstituted amide solvent (fatty acid dimethylamide), Halcomide M-8-10, at about 10% by weight. The formulation has good emulsification properties, low VOC content and is expected to have good pesticidal activity in the field.

Example 2

A formulation was prepared by conventional blending techniques consisting of Pyriproxyfen Technical at about 8% by weight, methyl oleate at about 72% by weight and a blend of non-ionic and anionic surfactants comprised of polyethylene-polypropylene glycol monobutyl ether, Toximul 8320, at about 12% by weight, tristyryl phenol ethoxylate with 16 moles of ethoxylation, Makon TSP 16, at about 6% by weight, and tristyryl phenol ethoxylate POE 16 phosphate ester, Stepfac TSP-PE, at about 2% by weight. The formulation has good emulsification properties, low VOC content and is expected to have good pesticidal activity in the field.

Example 3

A formulation was prepared by conventional blending techniques consisting of Pyriproxyfen Technical at about 11% by weight, a non-ionic/anionic surfactant blend comprised of 30% by weight of 60% active Ca alkylbenzenesulfonate in 2-ethyl hexanol and 70% by weight of 100% active fatty acid alkoxylate at about 12% by weight; methyl oleate at about 69% by weight, and a disubstituted amide solvent Agnique® KE 3658 (fatty acid dimethylamide) at about 8% by weight.

First, Pyriproxyfen Technical was dissolved into methyl oleate. Then, Agnique® KE 3658 and the non-ionic/anionic surfactant blend were added. The mixture was blended until a clear homogenous solution was obtained. The formulation has good emulsification properties. Samples stored for four months at −7° C., room temperature, 40° C., and 50° C. remained a clear, transparent liquid with no crystal formulation and no change in pyriproxyfen content. The samples also retained good emulsification properties.

Example 4

A formulation was prepared by conventional blending techniques consisting of Pyriproxyfen Technical at about 18% by weight, a blend of methyl oleate, methyl stearate, methyl palmitate and methyl linoleate (CE-1618 from Proctor & Gamble) at about 61% by weight, a tristyryl phenol ethoxylate with 16 moles of ethoxylation, Makon TSP 16, at about 9% by weight, and a disubstituted amide solvent (fatty acid dimethylamide), Halcomide M-8-10, at about 12% by weight. The formulation has good emulsification properties, low VOC content and is expected to have good pesticidal activity in the field.

Example 5

Robustness Study

To test whether the methyl oleate and disubstituted amide solvents can be replaced with equivalent materials from alternate suppliers without adverse effects, three samples made according to Example 3 were compared:

Sample 1: Methyl Oleate from Cognis® (Agnique® ME 181-U);

Disubstituted amide solvent from Cognis® (Agnique® KE 3658);

Sample 2: Methyl Oleate from Procter and Gamble®) (CE-1897);

Disubstituted amide solvent from Cognis® (Agnique®) KE 3658);

Sample 3: Methyl Oleate from Cognis® (Agnique® ME 181-U);

Disubstituted amide solvent from Stepan® (Hallcomid M-8-10);

Samples were put on stability studies and analyzed after storage at −7° C., room temperature, 40° C., and 50° C. for 1 month, 2 months, 3 months and 6 months.

The Experiment demonstrated that all three samples retained their appearance and activity. Pyriproxyfen assay detected about the same amount of the active (11.2-11.5%) for all three samples after storage at all tested conditions. No crystals formed in any of the samples. Also, the pH value of the formulations did not significantly change.

These results suggest that there are no significant differences between the samples and that they are stable at long storage conditions. Also, it appears that the source of methyl oleate and amide solvent is not critical.

Example 6

Performance Data for California Red Scale on Valencia Oranges, Citrus Species

A. Design and Methods

Valencia Oranges, citrus species were treated with one application of the Composition of the present invention and Comparative Pyriproxyfen Compositions. The treatment was applied by a foliar spray method. The treatment was applied as demonstrated in Table 1, with four replicates per treatment. "Comp. Compos." stands for "Comparative Pyriproxyfen Composition," and "Inven. Compos." stands for "Composition of the Present Invention".

TABLE 1

| Composition | Concentration (pounds active ingredient per gallon or % active ingredient wt/wt) | Composition Type | Application Rate (gram active ingredient per acre) |
| --- | --- | --- | --- |
| Untreated Control | 0 | N/A | N/A |
| Comp. Compos. 1 | 0.86 | Emulsifiable Concentrate | 50 |
| Comp. Compos. 2 | 35% | Wettable Powder | 50 |
| Comp. Compos. 3 | 0.75 | Capsule Suspension | 50 |
| Comp. Compos. 4 | 0.86 | Dispersible Concentrate | 50 |
| Inven. Compos. 5 From Ex. 3 | 0.86 | Emulsifiable Concentrate | 50 |

Treated plot size was 20 feet wide and 21 feet long; application volume was 1008.3 gallon per acre; mixture size was 42 gallons.

B. Results

Test plots were evaluated for California Red Scale (*Aonidiella aurantii*) at 0, 60, 90 and 120 days after treatment. Each tree replicate was randomly evaluated for 10 leaves and 10 fruit. Leaves were evaluated at 0, 60, 90 and 120 days after treatment; fruit was evaluated at 90 days and 120 days after treatment. The samples were evaluated for live viable scale and the total counts were divided by 10 to arrive at the average number of live scale for each replicate.

Also, phytotoxicity of the compositions to the citrus trees was evaluated at 7 days after the application. Phytotoxicity was rated on a 0 to 100 scale, with 0 being no damage and 100 being total plant death.

The results are summarized in Table 2.

TABLE 2

| Composition | Application Rate (gram active ingredient per acre) | Counts 0 days (leaves) | Counts 60 days (leaves) | Counts 90 days (leaves) | Counts 90 days (fruit) | Counts 120 days (leaves) | Counts 120 days (fruit) | Phytotoxicity 7 days |
| --- | --- | --- | --- | --- | --- | --- | --- | --- |
| Untreated Control | N/A | 0.00 | 0.00 | 0.35 | 0.83 | 1.83 | 1.90 | 0.00 |
| Comp. Compos. 1 | 50 | 0.00 | 0.00 | 0.00 | 0.03 | 0.43 | 0.18 | 0.00 |
| Comp. Compos. 2 | 50 | 0.00 | 0.00 | 0.08 | 0.00 | 0.33 | 0.23 | 0.00 |
| Comp. Compos. 3 | 50 | 0.00 | 0.00 | 0.00 | 0.10 | 0.13 | 0.15 | 0.00 |
| Comp. Compos. 4 | 50 | 0.00 | 0.00 | 0.00 | 0.05 | 0.33 | 0.20 | 0.00 |
| Inven. Compos. 5 From Ex. 3 | 50 | 0.00 | 0.00 | 0.03 | 0.03 | 0.68 | 0.45 | 0.00 |

No scale was noted on the leaves at the 60 days after treatment (DAT) evaluation. Counts were relatively low and all of the treatments were statistically equal to each other. At the 90 DAT evaluation, there were some numerical variations among the chemical treatments; however, chemical treatments were superior to the untreated control. The same trend was observed at the 120 DAT evaluation. Also, it was observed that at the 120 DAT evaluation, treatment with the Composition of the present invention produced numerically worse results than the treatment with the Comparative Pyriproxyfen Compositions, but this difference was not statistically significant. Nevertheless, the Composition of the present invention was significantly superior to the Untreated Control.

No phytotoxicity was observed with respect to either the Composition of the present invention or the Comparative Pyriproxyfen Compositions.

Thus, both the Inventive Composition and the Comparative Pyriproxyfen Compositions exhibited good control of California Red Scale on citrus in this Experiment.

Example 7

Performance Data on Navel Oranges, Citrus sp

A. Design and Methods

Navel Oranges, citrus species, were treated with the Composition of the present invention and Comparative Pyriproxyfen Compositions. The treatment was applied by foliar spray method. The treatment was applied as demonstrated in Table 3, with four replicates per treatment. "Comp. Compos." stands for "Comparative Pyriproxyfen Composition," and "Inven. Compos." stands for "Composition of the present invention".

TABLE 3

| Composition | Concentration (pounds active ingredient per gallon) | Composition Type | Application Rate (gram active ingredient per acre) |
|---|---|---|---|
| Untreated Control | 0 | N/A | N/A |
| Comp. Compos. 1 | 0.86 | Emulsifiable Concentrate | 50 |
| Comp. Compos. 2 | 0.75 | Capsule Suspension | 50 |
| Comp. Compos. 3 | 0.86 | Dispersible Concentrate | 50 |
| Inven. Compos. 4 From Ex. 3 | 0.86 | Emulsifiable Concentrate | 50 |
| Comp. Compos. 5 | 4.8 | Emulsifiable Concentrate | 50 |

Treated plot size was 20 feet wide and 16 feet long; application volume was 1099.2 gallon per acre; mixture size was 36 gallons.

C. Results

The test plots were evaluated for California Red Scale (*Aonidiella aurantii*) at 0, 60, 90 and 120 days after treatment. Each tree replicate was randomly evaluated for 10 leaves and 10 fruit. Leaves were evaluated at 0, 60, 90 and 120 days after treatment; fruit was evaluated at 90 days and 120 days after treatment. The samples were evaluated for live viable scale and the total counts were divided by 10 to arrive at the average number of live scale for each replicate.

Also, phytotoxicity of the compositions to the citrus trees was evaluated at 7 days after the application. Phytotoxicity was rated on a 0 to 100 scale, with 0 being no damage and 100 being total plant death.

The results are summarized in Table 4.

TABLE 4

| Composition | Application Rate (gram active ingredient per acre) | Counts 0 days (leaves) | Counts 60 days (leaves) | Counts 90 days (leaves) | Counts 90 days (fruit) | Counts 120 days (leaves) | Counts 120 days (fruit) | Phytotoxicity 7 days (leaves) |
|---|---|---|---|---|---|---|---|---|
| Untreated Control | N/A | 0.00 | 0.00 | 1.35 | 0.85 | 1.75 | 1.40 | 0.00 |
| Comp. Compos. 1 | 50 | 0.00 | 0.00 | 0.33 | 0.25 | 0.03 | 0.03 | 0.00 |
| Comp. Compos. 2 | 50 | 0.00 | 0.00 | 0.50 | 0.03 | 0.18 | 0.03 | 0.00 |
| Comp. Compos. 3 | 50 | 0.00 | 0.00 | 0.10 | 0.00 | 0.03 | 0.03 | 0.00 |
| Inven. Compos. 4 From Ex. 3 | 50 | 0.00 | 0.00 | 0.15 | 0.10 | 0.08 | 0.03 | 0.00 |
| Comp. Compos. 5 | 50 | 0.00 | 0.00 | 0.25 | 0.00 | 0.13 | 0.03 | 0.00 |

No scale was noted on the leaves at the 60 days after treatment (DAT) evaluation. Counts were relatively low and all of the treatments were statistically equal to each other. At the 90 DAT evaluation, there were some numerical variations among the chemical treatments with respect to leaves; however, chemical treatments were superior to the untreated control. The same trend was observed at the 120 DAT evaluation. Also, it was observed that at the 120 DAT evaluation, all of chemical treatments were essentially equal and statistically superior to the Untreated Control. Thus, the Composition of the present invention was significantly superior to the Untreated Control.

No phytotoxicity was observed with respect to either the Composition of the present invention or Comparative Pyriproxyfen Compositions.

Thus, both the Composition of the present invention and Comparative Pyriproxyfen Compositions exhibited good control of California Red Scale on citrus in this Experiment.

Example 8

Performance Data on for Oriental Fruit Moth on Plum

A. Design and Methods

Plum trees were treated with the Composition of the present invention and the Comparative Pyriproxyfen Compositions. The treatment was applied by foliar spray method. The treatment was applied as demonstrated in Table 5, with four replicates per treatment. "Comp. Compos." stands for "Comparative Pyriproxyfen Composition," and "Inven. Compos." stands for "Composition of the present invention".

TABLE 5

| Composition | Concentration (pounds active ingredient per gallon or % active ingredient wt/wt) | Composition Type | Application Rate (gram active ingredient per acre) |
|---|---|---|---|
| Untreated Control | 0 | N/A | N/A |
| Comp. Compos. 1 | 0.86 | Emulsifiable Concentrate | 50 |
| Comp. Compos. 2 | 35% | Wettable Powder | 50 |
| Comp. Compos. 3 | 0.75 | Capsule Suspension | 50 |
| Comp. Compos. 4 | 0.86 | Dispersible Concentrate | 50 |
| Inven. Compos. 5 From Ex. 3 | 0.86 | Emulsifiable Concentrate | 50 |

Treated plot size was 20 feet wide and 20 feet long; application volume was 100 gallon per acre; mixture size was 3 gallons.

D. Results

This trial was conducted in Northern California. Typically, Oriental Fruit Moths go to the shoot of young trees. This makes is easy to evaluate efficacy of candidate insecticides. Counts were made by evaluating shoot strike per tree at 14 days after the treatment. Phytotoxicity of the compositions to the plum trees was also evaluated at 14 days after the application. Phytotoxicity was rated on a 0 to 100 scale, with 0 being no damage and 100 being total plant death.

The results are summarized in Table 6.

TABLE 6

| Composition | Application Rate (gram active ingredient per acre) | Shoot strikes/tree 14 DAT | Phytotoxicity 14 DAT |
|---|---|---|---|
| Untreated Control | N/A | 3.5 | 0.0 |
| Comp. Compos. 1 | 50 | 1.5 | 0.0 |
| Comp. Compos. 2 | 50 | 0.5 | 0.0 |
| Comp. Compos. 3 | 50 | 0.5 | 0.0 |
| Comp. Compos. 4 | 50 | 0.8 | 0.0 |
| Inven. Compos. 5 From Ex. 3 | 50 | 0.3 | 0.0 |

Regarding Oriental Fruit Moth, at the 14 days after treatment evaluation, there were some numerical variations among the chemical treatments; however, chemical treatments were statistically superior to the untreated control. Also, it was observed that treatment with the Composition of the present invention produced numerically better results than the treatment with the Comparative Pyriproxyfen Compositions and was significantly superior to the Untreated Control.

No phytotoxicity was observed with respect to either the Composition of the present invention or the Comparative Pyriproxyfen Compositions.

Example 9

A formulation was prepared by conventional blending techniques consisting of pyriproxyfen technical at about 11%, a non-ionic/anionic surfactant blend comprised of 30% by weight of 60% active Ca alkylbenzenesulfonate in 2-ethyl hexanol and 70% by weight of 100% active fatty acid alkoxylate at about 12% by weight; methyl oleate at about 69% by weight, and a disubstituted amide solvent Agnique KE 3658 (fatty acid dimethyl amide) at about 8% by weight.

The formulation was tested for volatile organic compound content by an independent laboratory (Intertek Caleb Brett) using an approved California VOC testing method of thermal gravimetric analysis. The test was performed in triplicate under GLP (Good Laboratory Practices). The result for VOC content was 10.24% as an average. Thus this formulation meets the California requirement that all liquid agricultural pesticide products contain ≤20% VOCs.

Example 10

A formulation was prepared by conventional blending techniques consisting of pyriproxyfen technical at about 11%, a non-ionic/anionic surfactant blend comprised of 30% by weight of 60% active Ca alkylbenzenesulfonate in 2-ethyl hexanol and 70% by weight of 100% active fatty acid alkoxylate at about 12% by weight; methyl oleate at about 40% by weight, and ethyl hexyl lactate as co-solvent at about 19% weight. The formulation has good emulsification characteristics, low VOC content and is expected to have good efficacy.

We claim:

1. A low volatile organic compound (VOC) emulsifiable concentrate pesticidal composition comprising:
    a. about 11% by weight of pyriproxyfen;
    b. about 69% by weight of methyl oleate;
    c. about 12% by weight of a non-ionic/anionic surfactant blend; and
    d. about 8% by weight of a disubstituted amide;
    wherein the weight percentages are based on the total weight of the pesticidal composition.

2. The composition of claim 1 wherein the disubstituted amide is selected from the group consisting of N,N-dimethyloctanamide, N,N-dimethyldecanamide, and a blend thereof.

3. A ready-to-use product prepared from the composition of claim 1.

4. A method of treating plants, comprising applying a pesticidally effective amount of the composition of claim 1 to the plants.

5. The method of claim 4 wherein the plants are genetically modified plants.

6. A low volatile organic compound (VOC) emulsifiable concentrate pesticidal composition comprising:
    a. about 11% by weight of pyriproxyfen;
    b. about 69% by weight of methyl esters of $C_{16}$-$C_{18}$ fatty acids;
    c. about 12% by weight of a non-ionic/anionic surfactant blend; and
    d. about 8% by weight of a disubstituted amide;
    wherein the weight percentages are based on the total weight of the pesticidal composition.

7. The composition of claim 6 wherein the disubstituted amide is selected from the group consisting of N,N-dimethyloctanamide, N,N-dimethyldecanamide, and a blend thereof.

8. A ready-to-use product prepared from the composition of claim 6.

9. A method of treating plants, comprising applying a pesticidally effective amount of the composition of claim 6 to the plants.

10. The method of claim 9 wherein the plants are genetically modified plants.

* * * * *